(12) United States Patent
Guttman et al.

(10) Patent No.: US 6,489,157 B1
(45) Date of Patent: Dec. 3, 2002

(54) MEDIUM FOR CULTIVATING MICROORGANISMS

(75) Inventors: Harry J. Guttman, Silversprings, MD (US); James A. Ryan, Cincinnati, OH (US); Wendy Jo Davis-Hoover, Wyoming, OH (US)

(73) Assignee: The Government of the United States of America as represented by the Administrator of the U.S. Environmental Protection Agency, Washington, DC (US)

( * ) Notice: Subject to any disclaimer, the term of this patent is extended or adjusted under 35 U.S.C. 154(b) by 0 days.

(21) Appl. No.: 09/550,613

(22) Filed: Apr. 17, 2000

Related U.S. Application Data

(60) Provisional application No. 60/129,694, filed on Apr. 16, 1999.

(51) Int. Cl.$^7$ .................................................. C12N 1/20
(52) U.S. Cl. .................................. 435/253.6; 435/252.5
(58) Field of Search ....................................... 435/253.6

(56) References Cited

U.S. PATENT DOCUMENTS

| | | | | |
|---|---|---|---|---|
| 3,420,741 A | * | 1/1969 | Rogoff | |
| 5,597,484 A | * | 1/1997 | Tolley et al. | 435/262.5 |
| 6,156,545 A | * | 12/2000 | Blanche et al. | 435/86 |

* cited by examiner

*Primary Examiner*—Herbert J. Lilling
(74) *Attorney, Agent, or Firm*—Browdy and Neimark, P.L.L.C.

(57) ABSTRACT

A medium for culturing microorganisms in the presence of $Pb^{2+}$ uses as a phosphate component, an O-phosphate-L-amino acid, to provide a source of phosphate for the microorganisms so as to avoid precipitating lead.

6 Claims, 6 Drawing Sheets

MEDIUM FOR CULTIVATING MICROORGANISMS

CROSS-REFERENCE TO RELATED APPLICATIONS

The present invention claims priority from provisional application Serial No. 60/129,694, filed Apr. 16, 1999, the entire contents of which are hereby incorporated by reference.

FIELD OF THE INVENTION

The present invention relates to a medium for use in cultivating microorganisms that does not precipitate in the presence of lead.

BACKGROUND OF THE INVENTION

Quantitative study of $Pb^{2+}$ uptake in microorganisms is important for developing technologies to remove and/or stabilize $Pb^{2+}$ in soils and sediments. There have been several studies concerning $Pb^{2+}$ uptake (15), the effect of $Pb^{2+}$ on growth (8) and $Zn^{2+}$ uptake (13), chemical transformation of $Pb^{2+}$ by bacteria (2), and $Pb^{2+}$ associated with cells (1). These studies are conducted to study the interaction of $Pb^{2+}$ with organisms either as models for human-$Pb^{2+}$ interactions or for using organisms to remediate lead contaminated sites.

However, a direct and quantitative analysis of $Pb^{2+}$ by these and other studies has been frustrated by the insolubility of $Pb^{2+}$ precipitates because a quantitative analysis of $Pb^{2+}$ absorption or adsorption by bacteria requires that the cells be isolated in a manner which prevents interferences from $Pb^{2+}$, and $Pb^{2+}$ precipitates in the external medium when present in concentrations of generally less than 1 mM. If an insoluble $Pb^{2+}$ precipitate coexists with cells in the medium, the precipitate cannot be separated and removed without destroying the bacteria. Since the $Pb^{2+}$ precipitate is typically highly insoluble, it cannot be dissolved by simply increasing the volume of the washing solution used in standard centrifugation or filter washing methods.

Another problem is that $Pb^{2+}$ precipitate prevents accurate turbidity measurements (the quickest measure of cell density) because the precipitate scatters light, creating an artificially high cell density reading.

To avoid or minimize $Pb^{2+}$ precipitation, some workers have used very low concentrations of phosphate in minimal medium (10, 12, 13), or diluted rich media (e.g., ref. 8). The drawback to using these media is that they are limited to very low $Pb^{2+}$ concentrations, typically micromolar. If a microorganism accumulates $Pb^{2+}$ to a cytoplasmic concentration of 1–2 mM, this would readily deplete an extracellular concentration of 1 microM $Pb^{2+}$. Further, this variation of extracellular $Pb^{2+}$ concentration significantly complicates a quantitative analysis of $Pb^{2+}$ uptake kinetic data. Another drawback is that these media usually only support minimal cell densities. The limitation of low cell densities results from the small amount of time in exponential growth which has a high enough cell density, and, hence, a reasonable volume of culture, sufficient to detect quantitatively $Pb^{2+}$ associated with the bacteria.

Alternatively, to study the effects of $Pb^{2+}$ on bacteria and the chemical transformation of $Pb^{2+}$ by bacteria, many workers have used media containing lead precipitate. This precipitate can occur either initially (i.e., LB medium in ref. 8) or can be consequent with growth (e.g., defined citrate medium in reference 2). However, in both cases there is no developed method to quickly separate precipitate from intact cells, and thus these media cannot be used to quantity $Pb^{2+}$ uptake in bacteria.

SUMMARY OF THE INVENTION

It is an object of the present invention to overcome the aforementioned differences in the prior art.

It is another object of the present invention to provide a minimal medium which does not precipitate with concentrations of over 1 mM $Pb^{2+}$.

It is a further object of the present invention to provide a medium which has a source of phosphate for microorganisms, but which does not precipitate in the presence of $Pb^{2+}$.

According to the present invention, a minimal medium has been developed which does not precipitate with $Pb^{2+}$ in concentrations up to 25 mM and which supports growth of soil isolate up to typical minimal medial cell density of ~$3\times10^9$ CFU/mL and up to ~$8\times10^9$ CFU/mL when the glucose concentration is increased to 200 mM. The medium of the present invention uses a phosphate substitute to provide a source of phosphate for the bacteria which does not precipitate lead.

Of the compounds which can be used, O-phosphate-L-threonine is particularly preferred as a source of phosphate for the microorganisms which do not precipitate with $Pb^{2+}$.

DETAILED DESCRIPTION OF THE INVENTION

Figure 1:
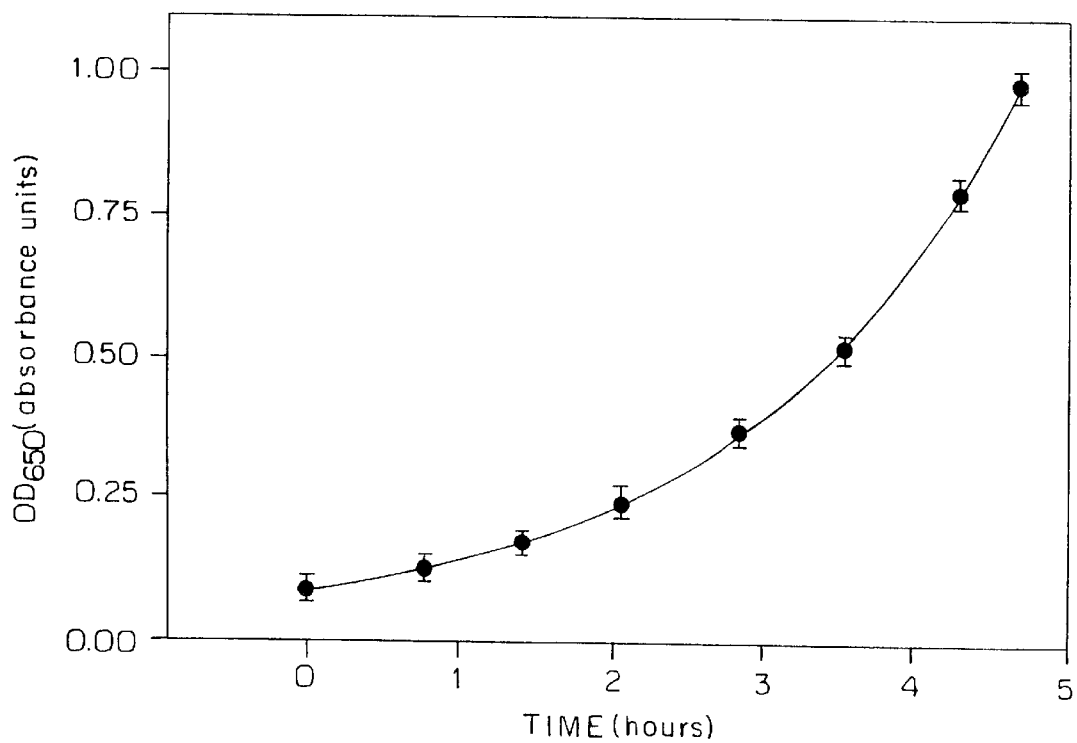
FIG. 1 shows a typical growth rate curve as $OD_{65C}$ as a function of time for an isolate of *P. aeruginoasa* CHL004 in BPTN at 29° C. Aerated at 200 rpm.

The present invention provides a liquid, minimal medium which does not precipitate with $Pb^{2+}$ and which supports growth of microorganisms. The most significant component of the medium is the replacement of phosphate by a phosphate source which does not precipitate with $Pb^{2+}$ when the $Pb^{2+}$ is present in concentrations up to 25 mM. The present invention eliminates interferences due to $Pb^{2+}$ precipitates in quantitative studies of Pb-organism interactions. For example, the present invention allows the use of optical density measurements, the quickest measure of cell density, to be used. Additionally, extracellular $Pb^{2+}$ can be readily washed away because there is no precipitate. Using the medium of the present invention allows studies and processes to be performed with high $Pb^{2+}$ concentrations in solution.

By replacing phosphate in conventional media with phosphorous compounds which do not precipitate $Pb^{2+}$, microorganisms can be grown in the presence of $Pb^{2+}$ without precipitating lead. There was no statistically significant change in growth rate constant or saturation cell density of CHL004 upon doubling the concentrations of all non-carbon source media components, indicating that there were no nutrient deficiencies. By varying the concentration of glucose and a phosphorus compound which does not precipitate in the presence of 25 mM $Pb^{2+}$, it was demonstrated that glucose is the limiting nutrient for the new medium and that the saturation cell density can be increased up to $OD_{650}$ ~5.0 by increasing the glucose concentration.

The growth rate constant of an isolate of CHL004 decreases as the concentration of $Pb(NO_3)_2$ is increased from zero to 1 mM. CFU/mL as a function of $OD_{650}$ for an isolate of CHL004 grown in BPTN was found to be very similar to and to have the same degree of linearity as an isolate of CHL004 grown in $BPTN+1\ mM+Pb(NO_3)^2$, making $OD_{650}$ as accurate a determination of cell density in the leaded medium as any other type of determination and indicating that precipitate is not consequent with cell growth.

Materials and Methods

Cell strains. *Pseudomonas aeruginosa* CHL004 is a soil isolate from the mouth of a pre-Civil War lead mine (15). Species level identification of CHL004 was perform by MIDI Labs, inc. using 16SrRNA full sequencing analysis, and with confirmatory identification by Microbial ID, Inc. using FAME analysis. *Pseudomonas aeruginosa* WBTC9020A was obtained from the UW-Madison Bacteriology Department Teaching collection and is descended from ATCC 10145. *Escherichia coli* MG1655 was obtained from Professor M. Thomas Record, Jr.'s laboratory at UW-Madison chemistry department and is descended from ATCC 47076.

Preparation of media and cultures. The composition of an example of a new, liquid, minimal media of the present invention is given in Table 1. BPTN minimal media is based on Neidhardt's original formulas of MOPS-buffered minimal media (9) and is prepared in a similar fashion.

TABLE 1

BPTN media components

| Component | Concentration (M) |
|---|---|
| Bis-Tris | 0.040 |
| Tricine | $4.0 \times 10^{-3}$ |
| $FeSO_4$ | $1.0 \times 10^{-5}$ |
| $NH_4NO_3$ | 0.010 |
| $K_2SO_4$ | $3.0 \times 10^{-4}$ |
| $Ca(NO_3)_2$ | $5.0 \times 10^{-7}$ |
| $Mg(NO_3)_2$ | $6.0 \times 10^{-4}$ |
| $KNO_3$ | $3.0 \times 10^{-3}$ |
| Micronutrients | 1X |
| Dextrose (glucose) | 0.020 |
| O-Phospho-L-threonine | $1.5 \times 10^{-3}$ |

The 1X micronutrient solution is composed of:
$3 \times 10^{-9}$ M $(NH_4)_6(Mo_7O_{24})$, $4 \times 10^{-7}$ M $H_3BO_3$, $3 \times 10^{-8}$ M $CoCl_2$, $1 \times 10^{-8}$ M $CuSO_4$, $8 \times 10^{-8}$ M $MnCl_2$, and $1 \times 10^{-8}$ M $ZnSO_4$ A 10× solution of the first nine components was used to simplify media preparation. The components were added from liquid or solid form in the order given in Table 1. In this procedure, the pH was adjusted using $HNO_3$ (not HCl) after adding Bis-Tris, and then checked again after the Tricine was added. A heptahydrate salt of $FeSO_4$ was used at $1.0 \times 10^{-2}$ M was used with appropriate amounts added to give the final 10× concentration. It is important that the $FeSO_4$ be made fresh so that oxidation to the Fe(III) state does not occur. After the remaining nine components were added, the pH was checked and adjusted if necessary. The 100× stock of glucose and a 100× stock of P-thr (pHed with NaOH to provide a source of $Na^+$) were prepared separately. To prepare 1×BPTN, these solutions were combined in appropriate dilutions and filter sterilized using a 0.2 micron PES filter immediately prior to inoculation.

All cultures were grown at 29° C. in a water bath incubator with shaking at a speed of 200 rpm. The cultures were inoculated with a saturated overnight culture in BPTN. Overnight cultures (~18 hours) were prepared from −80° C. freezer stocks. Data were typically obtained after approximately three or more doublings, and only data between an optical density at 650 nm ($OD_{650}$) of 0.1 and half the saturation cell density were used for analysis.

FIG. 1 shows a typical growth rate cure with $OD_{650}$ as a function of time for an isolate of *P. aeruginosa* CHL004 in BPTN at 29° C. aerated at 200 rpm. Each point represents a duplicate determination of $OD_{650}$. The reduced chi-squared for this fitting is 0.23, with the following best fit parameters and 68.3% confidence intervals, k=0.53 (0.52, 0.55), and a=0.08 (0.076, 0.085). Since the correlation coefficient between k and a is 0.98, these confidence intervals should be viewed as narrow estimates. Indeed, a larger standard deviation was found when averaging the growth rate constants from ten individual growth rate constant determinations.

Growth rate and saturation cell density studies. The $OD_{650}$ was measured using a Perkin Elmer Lambda 2 UV/VIS spectrometer. The cell path length was 10 mm. Duplicate 100 μL aliquots were taken from growing cultures and diluted with 900 microliters of a solution having a minimum concentration of 62 mM $NaNO_3$. The same diluent was used within a given growth rate curve. Sixty two mM $NaNO_3$ was determined to be isosmotic with BPTN. Osmolalities were determined using a Precision Instruments microOsmette freezing point depression osmometer calibrated at 0, 100, and 500 mOsm.

Growth rate data were fit to the first order rate equation $$OD_{650} = a \cdot e^{kt}$$

where a=pre-exponential factor k=growth rate constant, and t=time

The parameters a and k were floated in the fittings, and t was the independent variable. The saturation cell density was determined by measuring the maximum $OD_{650}$ of the culture.

Measurement of $Pb^{2+}$ concentrations. Two spectral lines on an inductively coupled plasma spectrometer (Thermo Jarrell Ash, ICAP 61E trace analyzer) were used to determine $Pb^{2+}$ concentrations. Samples were diluted into 1 M $HNO_3$ (prepared from trace metal grade $HNO_3$ (Fisher) to a $Pb^{2+}$ concentration between 0.5 and 20.0 μM. A four point line (linear correlation coefficient >0.9995) of $Pb^{2+}$ standards prepared in 1 M $HNO_3$ bracketed the range of $Pb^{2+}$ sample concentrations and was used to determine these $Pb^{2+}$ concentrations.

Data fittings and error analysis. Fittings were performed using NONLIN (7, 14) or the nonlinear function form regression in Sigma Plot (version 4.01).

The growth rate constants and saturation cell densities reported in FIGS. 2–5 are means of data collected from different cultures, typically performed on different days. Data points in FIGS. 2–5 represent the mean and standard deviation of duplicate or triplicate determinations, except for BPTN, where it is the mean of ten determinations of growth rate constants and six determinations for saturate cell densities. Differences between the means were tested using a t-test. The differences we considered to be statistically significant at a significance level of 0.05.

Figure 2:
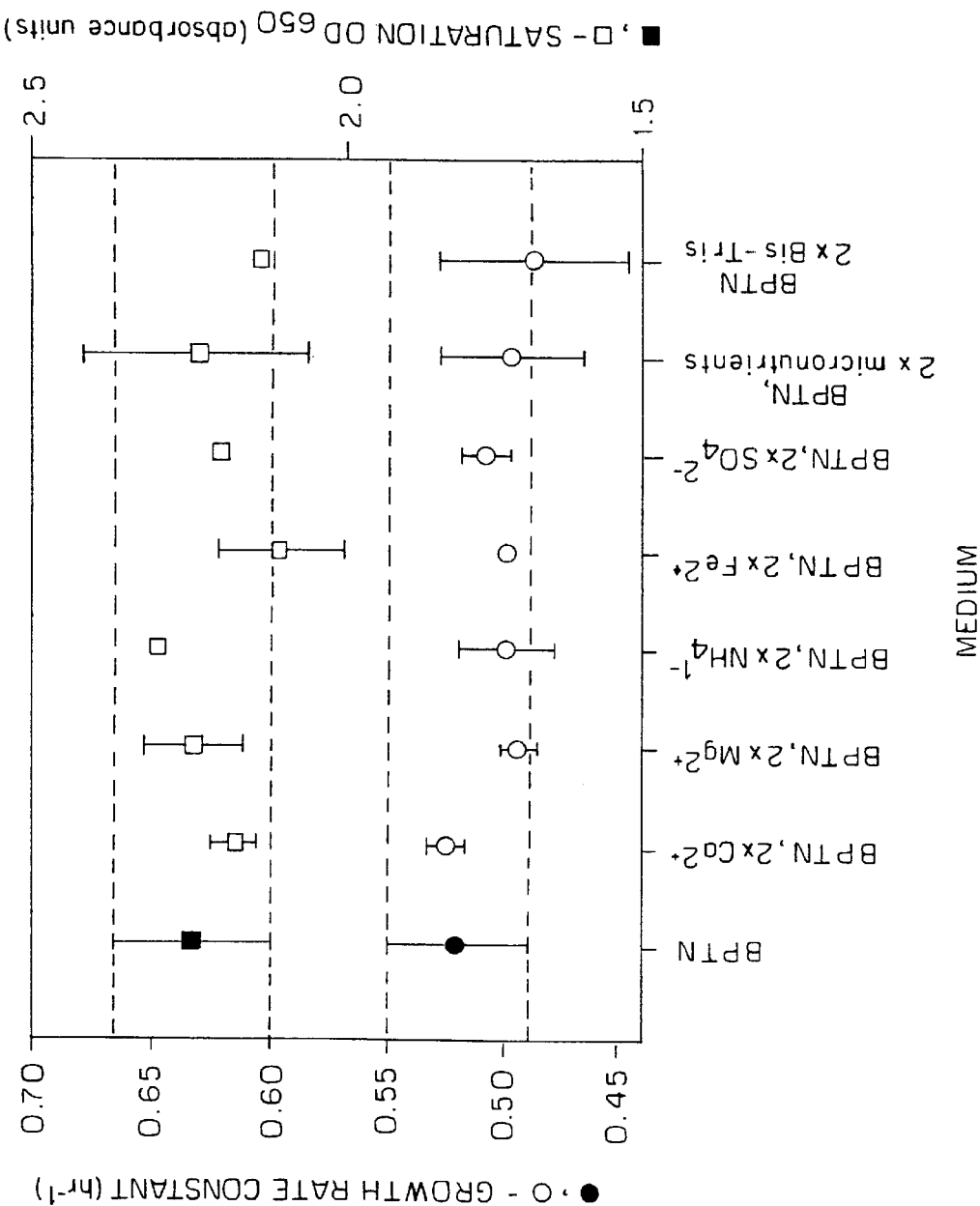
FIG. 2 shows growth rate constants and saturation cell densities of an isolate of CHL004 in BPTN and BPTN supplemented with twice the normal concentrations.

In FIG. 2, the growth rate constants and saturation cell densities of an isolate of CHL004 in BPTN and BPTN supplemented with twice the normal concentrations are shown. The final concentrations of the indicated components are as follows:

BPTN, $Ca^{2+}2\times$ has $1.0\times10^{-6}$ M $Ca(NO_3)_2$; BPTN has $2\times Mg^{2+}$ has $1.2\times10^{-3}$ M $Mg(NO_3)_2$; BPTN, $2\times NH_4$ has 0.020 M $NH_4NO_3$; BPTN, $2\times Fe^{2+}$ has $2.0\times10^{-5}$ M $FeSO_4$; BPTN, $2\times SO_4^{2-}$ has $6.0\times10^{-4}$ M $K_2SO_4$; BPTN, 2×micronutrients has 2×micronutrients; BPTN, 2×Bis-Tris has 0.080 M Bis-Tris.

Figure 5:
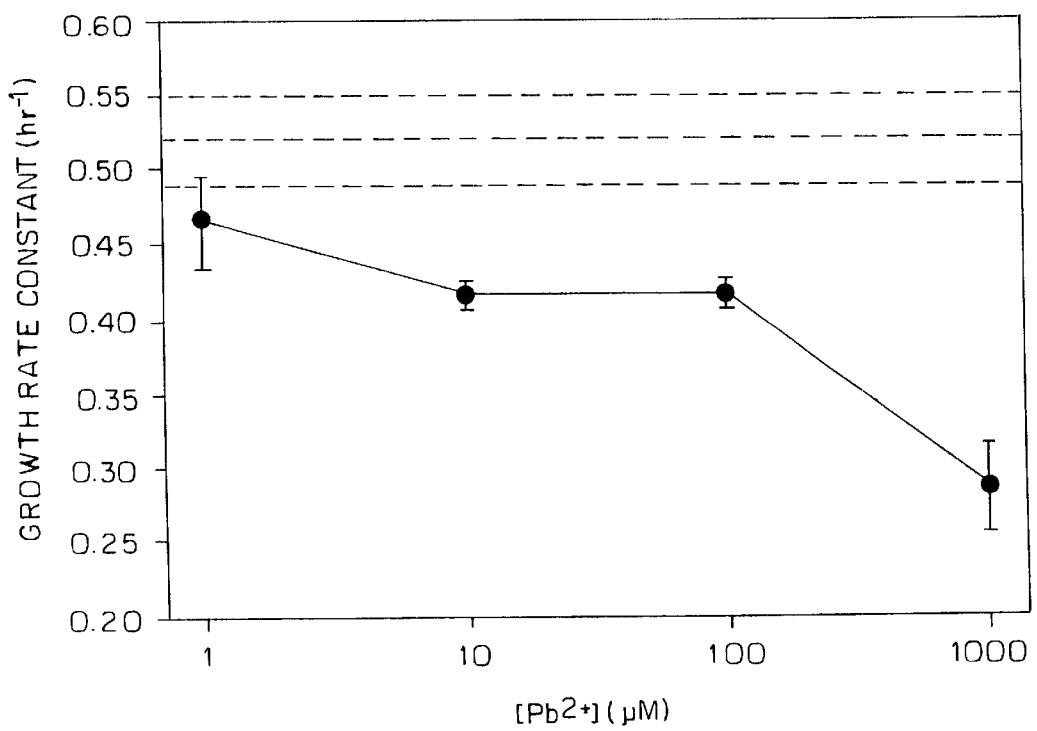
FIG. 5 shows the growth rate constant of an isolate of CHL004 as a function of $Pb^{2+}$ concentration added to BPTN.

In FIG. 5, the long dashed and short dashed lines are the growth rate constant and standard deviation, respectively, in BPTN without added $Pb(NO_3)_2$. Points represent the mean and standard deviation of duplicate or triplicate determinations, except for BPTN+100 microM $Pb(NO_3)_2$, which is the average and standard deviation of four determinations.

Preparation studies to find a phosphate substitute. Since phosphate is known to form highly insoluble complexes with $Pb^{2+}$ (11,17), the initial goal was to find a phosphate containing compound which did not precipitate with $Pb(NO_3)_2$. Table 2 shows the results of qualitative precipitation experiments. Except for P-thr, all of the solutions showed precipitation as judged visually by the presence of cloudiness immediately after adding $Pb(NO_3)_2$. Twenty four to 48 hours after the initial addition, all solutions except P-thr still had significant precipitate.

TABLE 2

Phosphate substitutes examined for $Pb^{2+}$ precipitation

| Precipitation | No Precipitation |
|---|---|
| O-Phospho-L-serine | |
| Sodium Phosphite | |
| N-(Phosphonomethyl)-glycine | |
| Phosphomycin | O-Phospho-L-threonine (P-thr) |
| Phosphocreatin | |
| Phospho(enol)pyruvate | |
| Glucose-1-phosphate | |
| Glucose-6-phosphate | |
| 3-Phosphoglyceric acid | |

Before $Pb(NO_3)_2$ was added from a 0.15 M stock solution to a final concentration of 1.5 mM, the pH of each 15.0 mM phosphate-substitute solution was adjusted using NaOH or $HNO_3$ and was between 5.6–6.9. Precipitation in these solutions was assessed visually, by the presence of cloudiness in the solution. All results were duplicated. Thus one skilled in the art can readily determine if a source of phosphorus microorganisms will precipitate lead.

A more quantitative examination of the solubility of $Pb(NO_3)_2$ in BPTN was conducted. It was found that $Pb(NO_3)_2$ was soluble in BPTN in an amount of 25 mM. Using ICAP trace metal analysis to measure $Pb^{2+}$ concentrations, there was found to be no statistically significant change in the $Pb^{2+}$ concentration before (24.0±0.6 mM, n-4) and after filtering (25.1±1.3 mM, n=4) through a 0.2 micrometer PES syringe filter. Therefore, it was concluded that all of the $Pb^{2+}$ was soluble.

Choice of buffer. Bis-Tris (bis-[2-hydroxyethyl]iminotris [hydroxymethyl]methane was chosen to buffer the pH in the medium because it has a $pK_a$ centered at the pH of choice, namely, 6.5 However, other buffers can be used, since preliminary experiments showed that several buffers at 40 mM did not precipitate with 1.5 mM $Pb(NO_3)_2$. If it is necessary to remove sulfate from the growth medium, buffers containing sulfate groups (such as ACES, N-[carbamoylmethyl]-2-aminoethanesulfonic acid; BES, N,N-bis[2-hydroxyethyle]2-aminoethanesulfonic acid; MOPS, 3-[N-morpholine]propanesulfonic acid; or MOPSO, 3-N-[morpholino]-2-hydroxypropanesulfonic acid) could also be used to act as both buffer and sulfate source. Indeed, Neidhardt et al (9) and Cayley et al. (4) found that sulfonated buffers can be used by some gram negative bacteria in such a way.

Growth studies without $Pb^{2+}$. Because BPTN or a similarly composed medium such as MOPS-buffered minimal medium in reference 9, has not been used with $P.$ $Aeruginosa$, growth rate studies were performed and the saturated cell densities were measured to ensure that the cells were not nutrient starved for the most important components. FIG. 1 shows data and a best fit curve for a typical growth rate determination of an isolate of CHL004 in BPTN. At 29° C., this medium also supports growth of typical laboratory strains of $P.$ $aeruginosa$ WBTC 9020A with a growth rate constant of 0.40±0.06/hr, and $E.$ $coli$ MG1655 with a growth rate constant of 0.31±0.03/hr.

The use of a phosphorus compound that does not precipitate lead as an inorganic phosphate source to these microorganisms is perhaps not unexpected, since bacteria such as $E.$ $coli$ and $S.$ $typhimurium$ can use sugar-based organophosphates as a source of inorganic phosphate (16). In Wanner (16), it is noted that organophosphates can be directly transported to the cytoplasm of $E.$ $coli$ and $S.$ $typhimurium$, or they can be hydrolyzed in the periplasm by phosphatases, after which the phosphate is transported to the cytoplasm. Additionally, it has now been demonstrated that O-phospho-L-serine can be used as a phosphate source by an isolate of CHL004.

FIG. 2 plots the growth rate constant and saturation cell density of an isolate of CHL004 component as a function of BPTN compared to a two-fold increase in concentration of the indicated BPTN components. Since there is no statistically significant effect on the growth rate constant and saturation cell density due to supplementation of the culture, it can be inferred that growth of an isolate of CHL004 in BPTN is neither nutrient limited nor poisoned by these media components.

To eliminate $PbCl_2$ precipitated in BPTN, nitrate has been substituted for chloride when used as an anion in the original MOPS-buffered minimal medium. At these higher nitrate concentrations, the nitrate may serve as a potential electron acceptor and interfere with oxygen respiration. However, there is no statistically significant effect on growth rate constant or saturation cell density when the nitrate, in the form of $NH_4NO_3$, concentration is increased by 65% (cf. FIG. 2). This result is consistent with previous studies (5,6) which show that oxygen inhibition of nitrate transport in $Pseudomonas$ $aeruginosa$ is immediate and complete at a very low level or oxygen saturation (0.2%) and independent of nitrate concentration. Therefore, it was concluded that the presence of ~13 mM nitrate in BPTN has no adverse effects on an isolate of CHL004.

Figure 3:
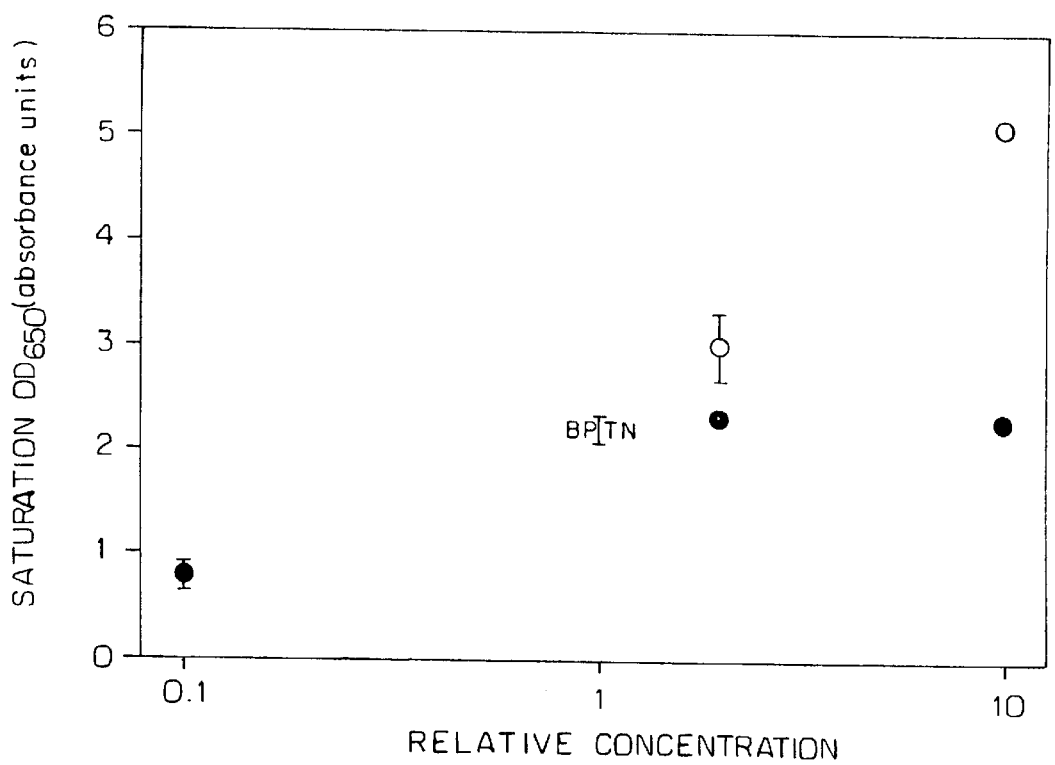
FIG. 3 shows $OD_{650}$ of saturated cell densities of an isolate of CHL004 as a function of relative concentrations of P-thr (○) and glucose (●) in BPTN.
Figure 4:
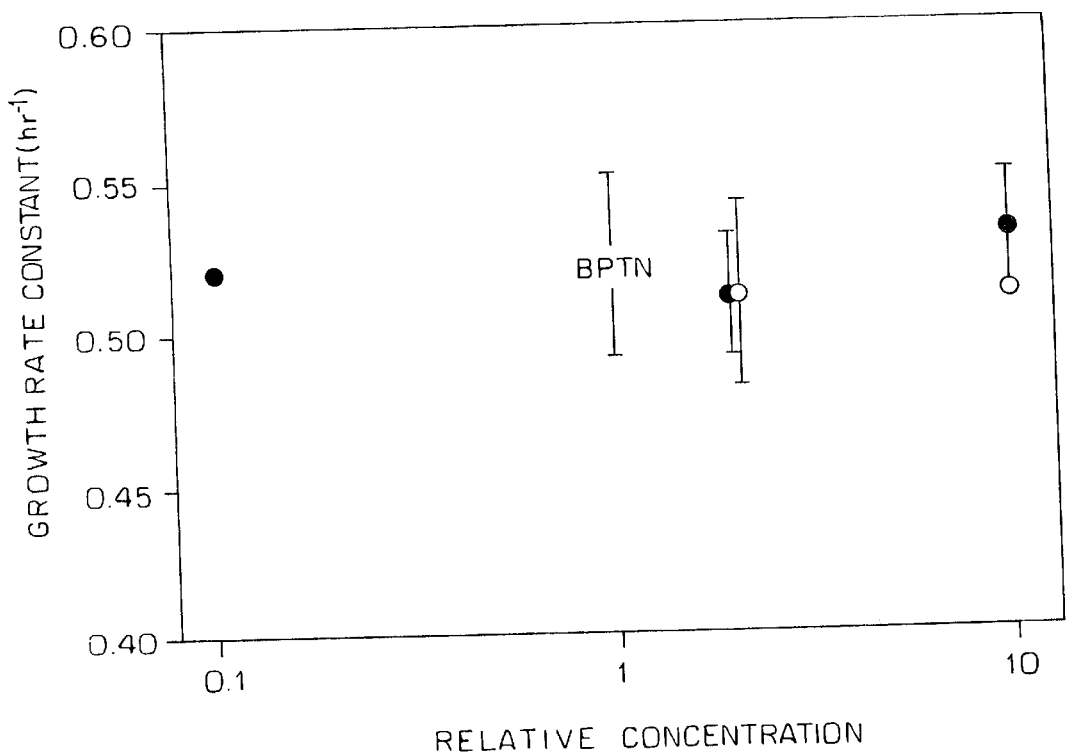
FIG. 4 shows the growth rate constant of an isolate of CHL004 as a function of relative concentration of P-thr (○), and glucose (●) in BPTN.

FIGS. 3 and 4 display the more extensive studies on variation of glucose and P-thr concentrations. In FIG. 3, the rise in saturated cell density with increasing glucose concentration suggests that the cell density BPTN can support is limited by the glucose concentration. However, P-thr can be made the limiting nutrient if its concentration is decreased to one tenth of its original concentration (0.15 mM).

FIG. 4 shows that the growth rate constant is the same within statistical significance for these same concentration variations in glucose and P-thr, suggesting that these variations do not significantly affect the fundamental metabolic processes responsible for exponential growth.

Growth in medium with $Pb(NO_3)_2$. FIG. 5 shows a decrease in growth rate constant of CHL004 in BPTN with increasing concentration. This demonstrates this strain's sensitivity to $Pb^{2+}$ in BPTN. The variances from the growth rate curve fittings for BPTN+1 mM $Pb(NO_3)_2$ are typically equal to or smaller than those for BPTN. A comparison of BPTN to BPTN+1 mM $Pb(NO_3)_2$ in FIG. 6 demonstrates that CFU/mL as a function of $OD_{650}$ are very similar, and it was found that a linear regression of both data sets gave a correlation coefficient of 0.991, indicating the same degree of linearity. A linear relationship between CFU/mL and $OD_{650}$ is expected if the extent of scattering is proportional to the cell density in the cell slurry. Since at an $OD_{650}$ of 1.0, in BPTN+1 mM $Pb(NO_3)_2$ are in early stationary phase, it was concluded that $OD_{650}$ measurements as a measure of cell density are equally accurate in BPTN and in BPTN+1 mM $Pb(NO_3)_2$ through exponential growth and at least into early stationary growth phase.

Figure 6:
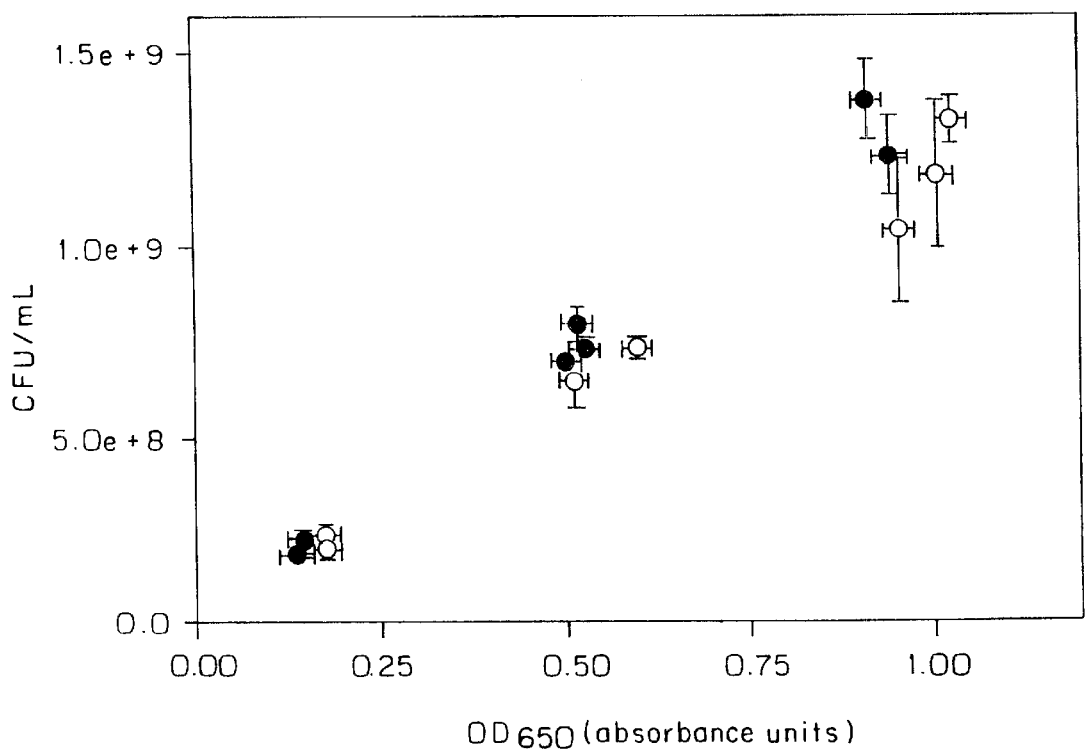
FIG. 6 shows CFU per mL of cell slurry as a function of $OD_{650}$ for an isolate of CHL004 frown in BPTN (○) and BPTN+1 mM $Pb(NO_3)_2$ (●).

The good quality of fittings of growth rate curves, the similarity of CFU/mL as a function of $OD_{650}$ in FIG. 6 and the high degree of linearity all suggest that precipitation does not occur with growth in BPTN+1.0 mM $Pb(NO_3)_2$. Indeed, visual inspection of the cultures and of saturated cell cultures grown in BPTN+1.0 mM $Pb(NO_3)_2$ showed no evidence of precipitate. This visual evidence contrasts with that of many workers who reported precipitate consequent with growth. Most notably, Blake et al. (2) report a visible brown-black insoluble precipitate consequent with growth of *Pseudomonas maltophilia* LB (lennox) broth, and Al-Aoukaty et al. (1) who report an insoluble pellet in their phosphate-rich media that is consequent with growth of *Pseudomonas fluorescens*.

The O-phospho-L-amino acids can be used in any conventional media as a source of phosphate for growth of microorganisms, especially where it is desired to eliminate precipitation of lead. There media are particularly well suited for bioremediation strategies, because the growth medium can be added to a lead contaminated site without causing further precipitation of lead in the soil. The less lead is precipitated, of course, the more is available for removal/remediation.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

REFERENCES

1. Al-Aoukaty, A, Appanna, V. D., and J. Huang. 1991. Exocellular and intracelluar accumulation of lead in *Pseudomonas fluorescens* ATTC 13525 is mediated by the phosphate content of the growth medium. FEMS Microbiol. Lett. 83:283–290.

2. Blake, R. C., Choate, D. M., Bardhan, S., Revis, N., Barton, L. L., and T. G. Zocco. 1993. Chemical transformation of toxic metals by a pseudomonas strain from a toxic waste site. Env. Tox. and Chem. 12:1365–1376.

3. Cayley, S., Lewis, B. A., Guttman, H. J., and M. Thomas Record, Jr. 1991. Characterization of the cytoplasm of *Escherichia coli* K-12 as a function of external osmolarity: Implications for protein-DNA interactions in vivo. J. Mol. Biol. 222:281–300.

4. Cayley, S., Record, M. T., Jr., and B. A. Lewis. 1989. Accumulation of 3- (N-morphilino)propanesulfonate by osmotically stressed *Escherichia coli* K-12. J. Bacteriol. 171:3597–3602.

5. Hernandez, D., Diaz, F. M., and J. J. Rowe. 1991. Nitrate transport and its regulation by $O_2$ in *Pseudomonas aeruginosa*. Arch. Biochem. and Biophys. 286:159–163.

6. Hernandez, D. and J. J. Rowe. 1987. Oxygen regulation of nitrate uptake in denitrifying *Pseudomonas aeruginosa*. Appl. Environ. Microbiol. 53:745–750.

7. Johnson, M. J. and S. G. Fraiser. 1985. Nonlinear least-squares analysis. Methods Enzymol. 117:301–342.

8. Levinson, H. S. and T. Mahler. 1988. Phosphatase activity and lead resistance in *Citrobacter freundii* and *Staphylococcus aureus*. FEMS Microbiol. Lett. 161:135–138.

9. Neidhardt, F. C., Bloch, P. L., and D. F. Smith. 1974. Culture medium for enterobacteria. J. Bacteriol. 119:736–747.

10. Nelson, Y. M., Lo. W., Lion, L. W., Shuler, M. L. and W. C. Ghiorse. 1995. Lead distribution in a simulated aquatic environment: Effects of bacterial biofilms and iron oxide. Wat. Res. 29:1934–1944.

11. Nraigu, J. O. 1973. Lead orthophosphates-II. Stability of chloropyromorphite at 25° C. Geochimica et Cosmochimica Acta. 37:367–377.

12. Poole, P. K., Williams, H. D., Downiw, J. A., and F. Gibson. 1989. Mutations affecting the cytochrome d-containing oxidase complex of *Escherichia coli* K12: Identification and mapping of a fourth locus, cydD. J. Gen. Microbiol. 135:1865–1874.

13. Rensing, C., Sun, Y., Mitra, B., and B. P. Rosen. 1998. Pb(II)-translocating P-type ATPases. J. Biol. Chem. 273:32614–32617.

14. Straume, M., Fraser-Cadoret, S. G., and M. L. Johnson. 1991. Least-squares analysis of fluorescence data. P. 177–240 In J. R. Lakoqicz (ed.), Topics in fluorescence spectroscopy, volume 2: Principles. Plenum Press, New York.

15. Vesper, S. J., Donovan-Brand, R., Paris, K. P., Al-Abed, S. R., Ryan, J. A., and W. J. Davis-Hoover. 1996. Microbial removal of lead from solid media and soil. Water, Air and Soil Pollution 86:207–219.

16. Wanner, B. L. 1996. Phosphorus assimilation and control of the phosphate regulon. p. 1357–1381. In F. C. Neidhardt (Editor in Chief), *Escherichia coli* and Salmonella: Cellular and molecular biology. ASM Press, Washington, D.C.

17. Zhang, P., Ryan, J. A. and L. T. Bryndzia. 1997. Pyromorphite formation from goethite adsorbed lead. Environ. Sci. Technol. 31:2673–2678.

What is claimed is:

1. A method for culturing microorganisms in the presence of $Pb^{2+}$ ions comprising culturing said microorganisms in a medium comprising at least one compound which can be used as a source of phosphorus for microorganisms but which does not precipitate $Pb^{2+}$ ions, wherein said medium does not form a precipitate in the presence of $Pb^{2+}$ ions.

2. The method according to claim 1 wherein at least one compound is O-phospho-L-threonine.

3. The method according to claim 1 wherein at least one compound is O-phospho-L-serine.

4. The growth medium according to claim 1 further comprising a buffer.

5. The growth medium according to claim 3 wherein the buffer is selected from the group consisting of buffers including at least one sulfate group.

6. The method according to claim 4 wherein the buffer is selected from the group consisting of Bis-Tris, ACES, BES, MOPS, and MOPSO.

* * * * *